United States Patent [19]

Hsu

[11] Patent Number: 4,740,524
[45] Date of Patent: Apr. 26, 1988

[54] ALPHA-HALOPYRUVATE OXIME

[75] Inventor: Adam C. Hsu, Lansdale, Pa.

[73] Assignee: Rohm and Haas Company, Philadelphia, Pa.

[21] Appl. No.: 864,046

[22] Filed: May 16, 1986

[51] Int. Cl.[4] ............................................. A01N 37/52
[52] U.S. Cl. ..................... 514/533; 514/477; 514/512; 514/530; 514/531; 514/547
[58] Field of Search ............. 560/35, 22, 168; 558/262; 514/477, 530, 512, 533, 531, 547

[56] References Cited

U.S. PATENT DOCUMENTS

| | | | |
|---|---|---|---|
| 3,629,239 | 12/1971 | Kitahonoki et al. | 560/35 |
| 3,742,036 | 6/1973 | Perronnet et al. | 560/168 |
| 4,052,192 | 10/1977 | Wilcox | 558/262 |
| 4,117,154 | 9/1978 | Stetter et al. | 560/168 |
| 4,425,360 | 1/1984 | Wolff et al. | 560/35 |

FOREIGN PATENT DOCUMENTS 2601867 7/1976 Fed. Rep. of Germany ...... 558/262

*Primary Examiner*—Donald B. Moyer
*Assistant Examiner*—Bruce D. Gray
*Attorney, Agent, or Firm*—Terence P. Strobaugh; William E. Lambert, III

[57] ABSTRACT

Alpha-halopyruvate oximes of the formula:

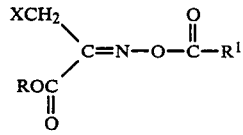

wherein R, R[1], and X are as defined herein having bactericidal and, fungicidal activity are disclosed.

20 Claims, No Drawings

ALPHA-HALOPYRUVATE OXIME

BACKGROUND OF THE INVENTION

This invention relates to novel alpha-halopyruvate oximes which exhibit activity as bactericides and fungicides, compositions containing these compounds and new methods of controlling bacteria and fungi with these compositions.

SUMMARY OF THE INVENTION

The novel alpha-halopyruvate oximes (I, infra) are represented by the formula:

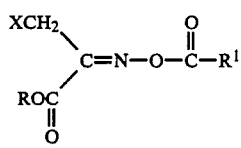   I wherein X is halo; R is alkyl, for example, lower alkyl of from 1 to 6 carbon atoms such as methyl, ethyl, propyl, butyl, pentyl, hexyl and the like; $R^1$ is alkyl, for example, straight or branched chain lower alkyl of from 1 to 15 carbon atoms, haloalkyl, for example, mono-, di- or trihalo lower alkyl, alkenyl, for example, lower alkenyl of from 2 to 6 carbon atoms, haloalkenyl, for example, halo lower alkenyl of from 2 to 6 carbon atoms, alkoxy for example, lower alkoxy of from 1 to 6 carbon atoms, aryl, aryloxy or aryloxyalkyl; for example, mononuclear and dinuclear aryl or aryloxy; substituted aryl, aryloxy or aryloxyalkyl wherein the substituents are selected from one or more halo, lower alkyl, lower alkoxy, halo lower alkyl or nitro substituents, aralkyl, for example, aryl lower alkyl and the like, arylalkenyl, for example, aryl lower alkenyl and the like, cycloalkyl, for example, cyclo lower alkyl of from 3 to 7 carbon atoms or lower alkylamino.

Halo includes chloro, fluoro, bromo, iodo and the like, aryl includes mononuclear aryl of from 6 to 10 nuclear atoms such as phenyl, naphthyl and the like, haloalkyl includes mono-, di- and trihaloalkyl groups such as chloromethyl, dichloromethyl, trifluoromethyl, dibromomethyl, 1,2-dichloroethyl and the like; alkyl includes methyl, ethyl, propyl, butyl, hexyl, heptyl, octyl, nonyl, decyl, undecyl, dodecyl and their isomers such as tert-butyl, iso-propyl, and the like; cycloalkyl includes cyclopropyl, cyclobutyl, cyclopentyl, cyclohexyl and the like; alkenyl includes ethenyl, propenyl, 1-butenyl, 2-butenyl, 2-methylpropenyl, 3,3-dimethyl-1-butenyl, 4-methyl-2-pentenyl, allyl, 1,3-butadiene, 1,4-pentadiene, 1,3,5-hexatriene, isopropenyl, 1-isobutenyl and the like; and haloalkenyl includes chloroallyl and the like; alkoxy includes methoxy, ethoxy, propoxy, butoxy, and the like; aryloxy includes phenoxy, naphthyloxy and the like; substituted aryl, axyloxy or aryloxyalkyl includes substituted phenyl and phenoxy such as 2, 3 or 4-bromophenyl or phenoxy; 2-, 3- or 4-trifluoromethylphenyl or phenoxy, 2,3 or 4-methyl- or methoxyphenyl or phenoxy; 2,4-, 2,6-, 3,4- or 3,6-dichlorophenyl or phenoxy; 2,6-difluorophenyl or phenoxy; 3 or 4-chloromethylphenyl or phenoxy, 4-cyanophenyl or phenoxy; 4-nitrophenyl or phenoxy, 4-chlorophenoxymethyl, 4-tert-butylphenyl or phenoxy; 2-acetyloxyphenyl or phenoxy and the like; aralkyl includes benzyl, phenethyl, alpha-methylbenzyl, 3-phenylpropyl, 2-phenylpropyl, and the like; aralkenyl includes styrene, cinnamyl(1-phenylpropene), 3-phenyl-propene, 2-phenyl-2-butene, 4-phenyl-2-butene, 4-phenylbutene, 5-phenyl-1,3-pentadiene, 5-phenyl-1,4-pentadiene, 3-phenyl-1,2-propadiene and the like and lower alkylamino includes methylamino, ethylamino, propylamino and the like.

Primarily because of their excellent bactericidal and fungicidal activity, compounds of the following formula are preferred:

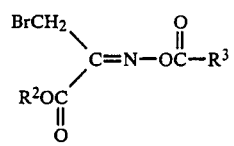   Ia wherein $R^2$ is lower alkyl of from 1 to 6 carbon atoms and $R^3$ is lower alkyl, lower alkenyl, phenyl lower alkyl, halophenyl, trifluoromethylphenyl, nitrophenyl or methylamino.

All of the compounds of Formula I (supra) (except when $R^1$ is alkylamino) may be prepared by the following process:

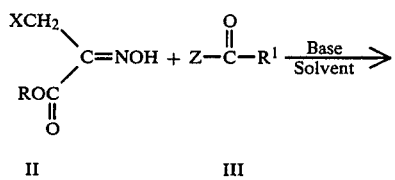

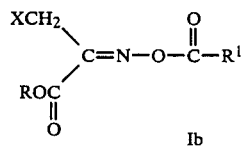   Ib where R, $R^1$, X are as defined above and Z is halo, preferably chloro.

This reaction may be carried out at a temperature in the range of from about 0° C. to about 80° C. Generally, the reaction is exothermic so in most cases no heating is required. The products of Formula Ib are isolated by known methods. Suitable solvents for conducting the reaction include inert organic solvents such as toluene, chloroform, methylene chloride, carbon tetrachloride and the like. Preferred bases for the reaction are organic tertiary bases such as triethylamine, pyridine and the like, or inorganic bases such as sodium bicarbonate, potassium hydrocarbonate and the like.

Those compounds wherein $R^1$ is alkylamino are prepared by treating the compound Formula II (supra) with an isocyanate (O=C=N—alkyl).

The compounds of Formula II (supra) are prepared by the following procedure:

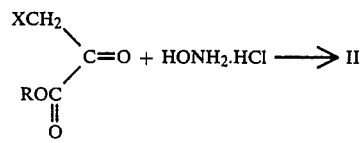

This reaction is conducted in an alkaline solution with or without mild heating.

The compounds of this invention can readily be utilized as bactericides and fungicides or combinations thereof in any locus, such as, for example, paper pulp processes, aqueous polymer dispersions, water-based paints, seed treatment applications and the like. In addition, these compounds and compositions containing them can function as fabric or leather preservatives, wood preservatives, cosmetic preservatives, soap additives, sanitizing agents, such as in laundry soaps and detergents, and preservatives for metal working compounds, such as emulsifiable cutting oils, preservatives for fuels, fiber spin finish biocides and the like.

In general, a locus subject to contamination by microorganisms can be protected in accordance with this invention by incorporating into the locus an alpha-halopyruvate oxime in an amount which is effective to control the microorganisms. The term "contamination" is meant to include any attack by microorganisms which leads to a chemical or physical breakdown or disintegration of the locus as well as the proliferation of the microorganisms within the locus without an accompanying deleterious effect. The exact amount of alpha-halopyruvate oxime required will, of course, vary with the medium being controlled, the particular alpha-halopyruvate oximes or compositions containing the alpha-halopyruvate oxime being employed and other factors. Typically, in a liquid medium, excellent control is obtained when the oximecarbamate is incorporated in the range of from about 0.01 to about 10,000 parts per million (ppm) or up to 95% based on the weight of the composition. A range of from about 0.05 to about 2,500 ppm is preferred.

The term "control" as employed in the specification and claims of this application is construed as the effect of any means which adversely affects the existence or growth of any living organism or microorganism. This effect may comprise a complete killing action, eradication, arresting in growth, inhibition, reduction in number or any combination thereof.

The alpha-halopyruvate oximes of this invention are useful as agricultural fungicides. As such, they are particularly valuable when formulated in a fungicial composition. Such compositions normally comprise an agronomically acceptable carrier and a alpha-halopyruvate oxime or mixture of alpha-halopyruvate oximes as the active agent. Where necessary or desirable, surfactants or other additives may be incorporated to give uniformly formulated mixtures. By "agronomically acceptable carrier" is meant any substance which can be utilized to dissolve, dispense or diffuse the chemical incorporated therein without impairing the effectiveness of the toxic agent and which does no permanent damage to such environment as soil, equipment and agronomic crops.

For use as agricultural fungicides, the compounds of the invention are usually taken up on an agronomically acceptable carrier or formulated so as to render them suitable for subsequent dissemination. For example, the alpha-halopyruvate oximes can be formulated as wettable powders, emulsion concentrates, dusts, granular formulations, aerosols or flowable emulsifiable concentrates. In such formulations the alpha-halopyruvate oxime is extended with a liquid or solid carrier and, when desired, suitable surfactants are likewise incorporated.

Compounds of this invention can be dissolved in a water-miscible liquid, such as ethanol, isopropanol, acetone, and the like. Such solutions are easily extended with water.

The alpha-halopyruvate oximes can be taken up on or mixed with a finely particled solid carrier as, for example, clays, inorganic silicates, carbonates, and silicas. Organic carriers can also be employed. Dust concentrates are commonly made wherein alpha-halopyruvate oximes are present in the range of from about 20% to about 80% by weight. For ultimate applications, these concentrates are normally extended with additional solids from about 1% to about 20% by weight.

Wettable powder formulations are made by incorporating the compounds of this invention in an inert, finely divided solid carrier along with a surfactant which may be one or more emulsifying, wetting, dispersing or spreading agents or blend of these. These alpha-halopyruvate oximes are usually present in the range of from about 10% to about 80% by weight and the surfactants are from about 0.5% to about 10% by weight. Commonly used emulsifying and wetting agents include polyoxyethylated derivatives of alkylphenols, fatty alcohols, fatty acids, and alkylamines, alkylarene sulfonates and dialkyl sulfosuccinates. Spreading agents include such materials as glycerol mannitan laurate and a condensate of polyglycerol and oleic acid modified with phthalic anhydride. Dispersing agents include such materials as the sodium salt of the copolymer of maleic anhydride and an olefin such as diisobutylene, sodium lignin sulfonate and sodium formaldehydenaphthalene sulfonates.

One convenient method for preparing a solid formulation is to impregnate the alpha-halopyruvate oxime toxicant onto the solid carrier by means of a volatile solvent, such as acetone. In this manner adjuvants, such as activators, adhesives, plant nutrients, synergists and various surfactants, can also be incorporated.

Emulsifiable concentrate formulations can be prepared by dissolving the alpha-halopyruvate oximes of this invention in an agronomically acceptable organic solvent and adding a solvent-soluble emulsifying agent. Suitable solvents are usually water-immiscible and may be found in the hydrocarbon, chlorinated hydrocarbon, ketone, ester, alcohol and amide classes of organic solvents. Mixtures of solvents may be employed. The surfactants useful as emulsifying agents may constitute from about 0.5% to about 10% by weight of the emulsifiable concentrate and may be anionic, cationic or nonionic in character. Anionic surfactants include alcohol sulfates or sulfonates, alkylarene sulfonates and sulfosuccinates. Cationic surfactant include fatty acid alkylamine salts and fatty acid alkyl quaternaries. Nonionic emulsifying agents include alkylene oxide adducts of alkylphenols, fatty alcohols, mercaptans and fatty acids. The concentration of the active ingredients may vary from about 10% to about 80%, preferably in the range of from about 25 to about 50%.

For use as a fungicidal agent, these compounds should be applied in an effective amount sufficient to exert the desired biocidal activity by techniques well-known in the art. Usually, this will involve the application of an effective amount of the alpha-halopyruvate oxime to the locus to be protected incorporated in an agronomically acceptable carrier. However, in certain situations, it may be desirable and advantageous to apply to compounds directly onto the locus to be protected without the benefit of any substantial amount of carrier. This is a particularly effective method when the physical nature of the alpha-halopyruvate oxime is such as to permit what is known as "low-volume" application; that is, when the compounds are in liquid form or substantially soluble in higher boiling solvents.

The application rate will vary depending upon the purpose for such application, the alpha-halopyruvate oxime being utilized, the frequency of dissemination and the like.

For use as agricultural bactericides and fungicides, dilute sprays can be applied at concentrations of from about 0.05 to about 20 pounds of the active alpha-halopyruvate oxime ingredient per 100 gallons of spray. They are usually applied at from about 0.1 to about 10 pounds per 100 gallons and preferably between about 0.125 to about 5 pounds per 100 gallons. In more concentrated sprays, the active ingredient is increased by a factor of 2 to 12. With dilute sprays, applications are usually made to the plants until run-off is achieved; whereas, with more concentrated or low-volume sprays, the materials are applied as mists.

As a fungicidal seed protectant, the amount of toxicant coated on the seed is usually at a dosage rate of from about 0.1 to about 20 ounces per hundred pounds of seed. As a soil fungicide the chemical can be incorporated in the soil or applied to the surface usually at a rate of from about 0.1 to about 50 lbs. per acre. As a foliar fungicide, the toxicant is usually applied to growing plants at a rate of from about 0.25 to about 10 lbs. per acre.

The composition can also be added to transplant water or employed as dips or soaks for vegetative parts employed in propagation, such as seeds, tubers, roots, seedlings, and the like, so as to disinfect and/or provide residual protection from nematodes, soil insects (and mites) and via systemic uptake, foliar pests. The application rate can be from about 0.5 to about 50 pounds per acre; however, higher rates can also be used. The preferred rate is from about 1 to about 25 pounds per acre. For soil incorporation, the compounds of this invention can be mixed with the soil at a rate of about 1 to about 100 ppm of active ingredient.

The compounds of this invention may be utilized as the sole biocidal agents or they may be employed in conjunction with other fungicides, bactericides, algaecides, slimicides, insecticides, miticides, or with other comparable pesticides.

The following examples illustrate this invention:

EXAMPLE 1

Ethyl 3-Bromo-2-(4-chlorobenzoyloximino)propanoate

To the mixture of ethyl 3-bromo-2-(hydorxyimino)-propanoate (3 g, 14.3 mmole) and 4-chlorobenzoyl chloride (2.75 g, 15.71 mmole) in dry methylene chloride (100 ml) at 0° to 5° C. with stirring, was slowly added dry pyridine (1.2 g, 15.18 mmole). After addition, the reaction mixture was stirred at room temperature for one hour. The reaction mixture was diluted with 50 ml of methylene chloride and washed with water and brine. The organic layer was dried with magnesium sulfate and the solvent evaporated to afford 5.0 g (99% yield) of ethyl 3-bromo-2-(4-chlorobenzoyloximino)-propanoate as a white solid, m.p. 82°-84.5° C.

EXAMPLE 2

Ethyl 3-Bromo-2-(methacryloyloximino)propanoate

Ethyl 3-bromo-2-(hydroxyimino)propanoate (4.0 g, 19 mmole) and methacryloyl chloride (2.18 g, 20.8 mmole) in methylene chloride (100 ml) were treated with dry pyridine (1.66 g, 21 mmole). After a workup as in Example 1, 4.42 g (84% yield) of ethyl 3-bromo-2-(methacryloyloximino)propanoate was obtained as an oil. NMR and IR spectra confirm the structure.

EXAMPLE 3

Ethyl 3-Bromo-2-(N'methylcarbamoyloximino)propanoate

To a solution of ethyl 3-bromo-2-(hydroxyimino)-propanoate (4.0 g, 19 mmole) in methylene chloride (25 ml) was added at room temperature, methylisocyanate (5.12 g, 95 mmole, 5 equivalents) and 15 drops of triethylamine. The reaction mixture was stirred at room temperature for 48 hours. The volatiles were evaporated under reduced pressure to afford 5.56 g of ethyl 3-bromo-2-(N'-methylcarbamoyloximino)propanoate as a light yellow solid, m.p. 90°-96° C.

EXAMPLE 4

Ethyl 3-Bromo-2-(4-methylbenzoyloximino)propanoate

To a mixture of ethyl 3-bromo-2-hydroxyimino)-propanoate (4 g, 19 mmole), and 4-methylbenzoyl chloride (3.23 g, 20.9 mmole) in dry methylene chloride (80 ml) at 0° to 5° C. with stirring, was added dry pyridine (1.65 g, 20.9 mmole) from a syringe. After addition, the reaction mixture was stirred at room temperature for two more hours. The reaction mixture was diluted with 50 ml of methylene chloride and washed with water and brine. The organic layer was dried over magnesium sulfate. The solvent was evaporated to afford 5.51 g (88% yield) of ethyl 3-bromo-2-(4-methylbenxoyloximino)propanoate as a white solid, m.p. 94°-96° C.

By following substantially the procedure described in Examples 1-4 and by substituting the appropriate starting material, the following compounds are prepared. The following formula taken together with Table I illustrate the compound. Table II is a list of the NMR data for the products of Examples 5-39.

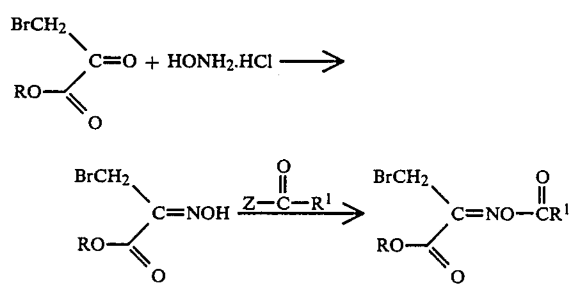

TABLE I

| Example No. | R | $R^1$ | Physical Data |
|---|---|---|---|
| 5 | Et | $-CH_2CH_3$ | oil |
| 6 | Et | $-OCH_3$ | oil |
| 7 | Et | $-CH=CH-C_6H_5$ | mp 113°-115° C. |
| 8 | Et | $-CH_2Cl$ | oil |
| 9 | Et | —cyclohexyl | oil |
| 10 | Et | $-CH_2C_6H_5$ | oil |
| 11 | Et | 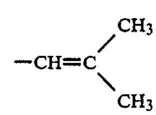  | oil |
| 12 | Et | $-C_{11}H_{23}-\underline{n}$ | oil |
| 13 | Et | $-CH_2CH_2C_6H_5$ | oil |

TABLE I-continued

| Example No. | R | R¹ | Physical Data |
|---|---|---|---|
| 14 | Et | —CHCH₃ <br> ‖ <br> Cl | oil |
| 15 | Et | —CH₂CH₂Cl | oil |
| 16 | Et | —C₆H₄—4-CH₃ | oil |
| 17 | Et | —CH₃ | oil |
| 18 | Et | —CH=CH₂ | oil |
| 19 | Et | —CH=CHCH₃ | oil |
| 20 | Et | —C₆H₄—4F | mp 90°-94° C. |
| 21 | Et | —C₆H₄—2CH₃ | oil |
| 22 | Et | —C₃H₇—n | oil |
| 23 | Et | —C₄H₉—n | oil |
| 24 | Et | —C₆H₄—3CH₃ | mp 56°-59° C. |
| 25 | Et | —C₅H₁₁—n | oil |
| 26 | Et | —C₆H₄—4OCH₃ | mp 65°-75° C. |
| 27 | Et | —C₆H₄—3OCH₃ | oil |
| 28 | Et | —C₆H₄—3CF₃ | oil |
| 29 | Et | —C₆H₄—4NO₂ | mp 119°-124° C. |
| 30 | Et | —C₆H₅ | mp 87°-89° C. |
| 31 | Et | —C₆H₄—4Br | mp 95°-98° C. |
| 32 | CH₃ | —C₆H₄4Cl | — |
| 33 | CH₃ | —C₆H₄—4-CH₃ | — |
| 34 | Et | —C₆H₁₃—n | oil |
| 35 | Et | —C₁₅H₃₁—n | mp 42°-45° C. |
| 36 | Et | —C₆H₄—3Cl | mp 95-97° C. |
| 37 | Et | —C₆H₄—2Cl | — |
| 38 | Et | —C₆H₃—3,4Cl₂ | mp 75°-78° C. |
| 39 | Et | —C=C(Cl)(Cl) with Cl | — |
| 40 | Et | —O—C₆H₅ | oil |
| 41 | Et | —O—CH₂—C₆H₅ | mp 60°-62° C. |
| 42 | Et | —cyclopropyl | oil |

TABLE II

NMR spectra were obtained in CDCl₃ solution on Varian T-60 and EM-360 instruments, with tetramethylsilane as the internal reference. Peaks positions (chemical shifts) are expressed in ppm (δ) downfield from tetramethylsilane.

| Exp. No. | Chemical Shifts (ppm or δ) |
|---|---|
| 5 | 4.75 to 4.22(4H, m, CH₂Br & OCH₂); 2.62 (2H, q, J=8 Hz, COCH₂; 1.58 to 1.00 (6H, m, 2 CH₃) |
| 6 | 4.70 to 4.24 (4H, m, CH₂Br & OCH₂); 4.00 (3H, s, OCH₃); 1.40 (3H, t, CH₃) |
| 7 | 7.52 (5H, br. s, arom. H); 7.98 & 6.64 (2H, ABq, JAB= 15 Hz, vinyl H); 4.65 to 4.20 (4H, m, CH₂Br & OCH₂); 1.38 (3H, t, CH₃) |
| 8 | 4.82 to 4.26 (6H, m, CH₂Br, OCH₂ & CH₂Cl); 1.38 (3H, t, CH₃) |
| 9 | 4.78 to 4.10 (4H, m, CH₂Br & OCH₂); 2.90 to 1.00 (14H, m) |
| 10 | 7.45 (5H, s, arom. H); 4.60 to 4.15 (4H, m, CH₂Br & OCH₂); 3.86 (2H, s, CH₂); 1.34 (3H, t, CH₃) |
| 11 | 6.02 (1H, br.s, vinyl H); 4.80 to 4.20 (4H, m, CH₂Br & OCH₂); 2.30 (3H, s, CH₃); 2.10 (3H, s, CH₃); 1.42 (3H, t, CH₃) |
| 12 | 4.70 to 4.20 (4H, m, CH₂Br & OCH₂); 2.80 to 1.10 (23H, m); 0.80 (3H, t, CH₃) |
| 13 | 7.30 (5H, br. s, arom. H); 4.70 to 4.20 (4H, m, CH₂Br & OCH₂); 3.24 to 2.62 (4H, m, CH₂CH₂); 1.32 (3H, t, CH₃) |
| 14 | 5.00 to 4.14 (4H, m, CH₂Br & OCH₂); 1.80 (3H, d, J=6 Hz, CH₃); 1.40 (3H, t, CH₃) |
| 15 | 5.00 to 4.20 (4H, m, CH₂Br & OCH₂); 3.94 (2H, t, CH2Cl); 3.10 (2H, t, COCH₂); 1.40 (3H, t, CH₃) |
| 16 | 8.10 TO 7.38 (4H, ABq, JAB=8 Hz, arom. H); 4.69 (2H, s, CH₂Br); 4.68 to 4.30 (2H, m, OCH₂); 2.44 (3H, s, CH₃); 1.40 (3H, t, CH₃) |
| 17 | 4.80 TO 4.25 (4H, m, CH₂Br & OCH₂); 2.30 (3H, s, CH₃); 1.38 (3H, t, CH₃) |
| 18 | 6.80 to 6.20 (3H, m, vinyl H); 4.70 to 4.20 (4H, m, CH₂Br & OCH₂); 1.36 (3H, t, CH₃) |
| 19 | 7.68 to 6.98 (1H, m, beta-vinyl H); 6.34 to 5.90 (1H, m, alpha-vinyl H); 4.74 to 4.18 (4H, m, CH₂Br & OCH₂); 2.10 to 1.76 (3H, m, CH₃); 1.35 (3H, t, CH₃) |
| 20 | 8.60 to 7.00 (4H, m, arom. H); 4.85 to 4.20 (4H, m, CH₂Br & OCH₂); 1.42 (3H, t, CH₃) |
| 21 | 8.30 to 7.20 (4H, m, arom. H); 4.70 to 4.30 (4H, m, CH₂Br & OCH₂); 2.68 (3H, s, CH₃); 1.40 (3H, t, CH₃) |
| 22 | 4.74 to 4.20 (4H, m, CH₂Br & OCH₂); 2.54 (2H, t, CH₂); 2.10 to 1.50 (2H, m, CH₂); 1.40 (3H, t, CH₃); 1.02 (3H, t, CH₃) |
| 23 | 4.70 to 4.15 (4H, m, CH₂Br & OCH₂); 2.58 (2H, t, CH₂); 2.00 to 1.20 (7H, m); 0.95 (3H, t, CH₃) |
| 24 | 8.20 to 7.35 (4H, m, arom. H); 4.76 to 4.28 (4H, m, CH₂Br & OCH₂); 2.44 (3H, s, CH₃); 1.40 (3H, t, CH₃) |
| 25 | 4.74 to 4.12 (4H, m, CH₂Br & OCH₂); 2.74 to 2.06 (2H, m, CH₂); 2.00 to 0.55 (12H, m) |
| 26 | 8.10 to 7.02 (4H, ABq, JAB=9 Hz, arom. H); 4.80 to 4.20 (4H, m, CH₂Br & OCH₂); 3.92 (3H, s, OCH₃); 1.40 (3H, t, CH₃) |
| 27 | 7.90 to 7.10 (4H, m, arom. H); 4.80 to 4.30 (4H, m, CH₂Br & OCH₂); 3.95 (3H, s, OCH₃); 1.40 (3H, t, CH₃) |
| 28 | 8.80 to 7.60 (4H, m, arom. H); 4.90 to 4.30 (4H, m, CH₂Br & OCH₂); 1.40 (3H, t, CH₃) |
| 29 | 8.42 (4H, br.s, arom. H); 4.80 to 4.24 (4H, m, CH₂Br & OCH₂); 1.44 (3H, t, CH₃) |
| 30 | 8.70 to 7.40 (5H, m, arom. H); 4.90 to 4.20 (4H, m, CH₂Br & OCH₂); 1.40 (3H, t, CH₃) |
| 31 | 8.20 to 7.56 (4H, m, arom. H); 4.80 to 4.30 (4H, m, CH₂Br & OCH₂); 1.40 (3H, t, CH₃) |
| 32 | 8.04 to 7.48 (4H, ABq, JAB=8 Hz, arom. H) 4.52 (2H, s, CH₂Br); 4.00 (3H, s, OCH₃) |
| 33 | 8.00 to 7.30 (4H, ABq, JAB=8 Hz, arom. H); 4.52 (2H, s CH₂Br); 3.96 (3H, s, OCH₃); 2.42 (3H, s, CH₃) |
| 34 | 4.54 (2H, s, CH₂Br); 4.46 (2H, q, OCH2; 2.84 to 2.36 (2H, m, COCH₂—); 2.12 to 1.16 (11H, m); 1.00 (3H, t, CH₃) |
| 35 | 4.68 to 4.34 (4H, m, CH₂Br & OCH₂); 2.82 to 2.40 (2H, m, COCH₂—); 1.60 to 1.10 (29H, m); 0.97 (3H, t, CH₃) |
| 36 | 8.34 to 7.18 (4H, m, arom. H); 4.82 to 4.30 (4H, m, CH₂Br & OCH₂); 1.52 (3H, t, CH₃) |
| 37 | 8.10 to 7.30 (4H, m, arom. H); 4.74 to 4.24 (4H, m, CH₂Br & OCH₂); 1.50 (3H, t, CH₃) |
| 38 | 8.46 to 7.55 (3H, m, arom. H); 4.86 to 4.34 (4H, m, CH₂Br & OCH₂); 1.56 (3H, t, CH₃) |
| 39 | 4.86 to 4.26 (4H, m, CH₂Br & OCH₂); 1.52 (3H, t, CH₃) |
| 40 | 7.60 to 7.00 (5H, br.s, arom. H); 4.68 to 4.20 (4H, m, CH₂Br & OCH₂); 1.34 (3H, t, CH₃) |
| 41 | 7.40 (5H, s, arom. H); 5.25 (2H, s, CH₂); 4.60 to 4.20 (4H, m, CH₂Br & OCH₂); 1.36 (3H, t, CH₃) |
| 42 | 4.70 to 4.18 (4H, m, CH₂Br & OCH₂); 2.10 to 0.85 (8H, m, CH₃ & cyclopropyl) |

The following test methods were employed to determine the various activities of those compounds.

I. Description of Biocide Test Procedure

1. A minimum inhibitory concentration (MIC) value is obtained using a broth, two-fold serial dilution test performed as follows: A stock solution or dispersion of the test compound, typically at a concentration of 1%, is made in an organic solvent, such as acetone. A volume of the stock solution is dispensed into culture media to give an initial starting test concentration of 250–500 ppm compound.

When the test is ready to be done, each vessel in the dilution series, except the first vessel, contains an equal volume of compound free broth. The first vessel contains twice the volume of broth with the starting concentration of test compound. One half of the broth from the first vessel is transferred to the second vessel. After being mixed, one half the resulting volume is removed from the second vessel and transferred to the third vessel. The entire cycle is repeated 8 to 12 times, depending on the number of dilutions desired. At the end of the series of dilutions, each succeeding vessel in the series has one half the concentration of test compound the previous vessel has.

Each vessel is then inoculated with a cell suspension of the appropriate test organism. Bacteria are grown in broth and fungi or agar slants, for a time and at a temperature appropriate to the species being tested. At the end of the growth period, the broth is vortexed to disperse the cells. In the case of fungi, the spores are harvested by pipetting water onto the salt and dislodging the spores with a sterile loop. The cel/spore suspension is standardized by controlling incubation time and temperature and the volume of the diluent. The suspension is then used to inoculate the vessels containing the broth compound. The vessels are then incubated at the appropriate temperature. After the incubation, the vessels are examined for growth/no growth. The minimum inhibitory concentration (MIC) is defined as the lowest concentration of compound that results in complete inhibition of growth of the test organism.

2. The speed of kill test measures loss of cell viability in an aqueous suspension of bacterial cells as a function of time when these cells are contacted with a defined concentration of test compound in the water. This is done by taking aliquots of the cell suspensions at the appropriate time interval and assaying the number of viable cells per milliliter by plate count or most probable number (MPN) methodology. These measurements are done on the cell suspensions containing test compound and on control suspensions containing no test compound. The viable cell counts of the test and control samples are then compared to determine cell death.

The test is set up by first dissolving the compound in an organic solvent, such as acetone, to make up a stock solution. This stock solution is typically at 1% concentration. The stock solution is then dispensed into sterile, synthetic hard water, typically at 200 ppm hardness expressed as $CaCO_3$, to give a final concentration of test compound of 100 ppm.

The inoculum is prepared by growing the bacteria on a slant for 24 hours and then harvesting the cells into phosphate buffer. To start the test at zero time, one volume of bacterial inoculum is added to 100 volumes of test solution containing compound at the final test concentration.

At appropriate time intervals, ranging from 10 min to 24 hrs, aliquots of all the test samples and controls are assayed for viable cell count, in colony forming units (CFU)/ml.

The results are calculated in terms of $log_{10}$ reduction in CFU/ml compared to aqueous control. This is done by taking the logarithm base 10 of the CFU/ml for the aqueous control count. One log reduction corresponds to 90% kill, 2 logs reduction corresponds to 99% kill, 3 logs reduction corresponds to 99.9% kill, etc.

Tested Organisms for "Biocides":
Bacteria:
  *Pseudomonas fluorescens*
  *Pseudomonas aeruginosa*
  *Staphylocoecus aureus* and *Escherichia coli*
Fungi:
  *Aspergillis niger*
  *Candida albicans*
  *Aureobasidium pullulans*
Tested Diseases for "Fungicides":
  1. Wheat Leaf Rust (*Puccinia graminis*)
  2. Tomato Late Blight (*Phytophthora infestans*)
  3. Wheat Powdery Mildew (*Erysiphe graminis*)
  4. Cucumber Downey Mildew (*Pseudoperonspora cubensis*)
  5. Rice sheath Blight (*Rhizoctonia Solani*)
  6. Rice Blast (*Pyricularia oryzae*)

Description of Fungicides Test Method

Wheat Leaf Rust (*Puccinia graminis*)

Wheat seedlings cultivar 'Fielder' are grown in rediearth and used for screening about seven days after planting. The seedlings are fertilized with liquid-M prior to use. The spore suspension is prepared by rehydrating from spores (from deep freeze ($-20°$ C.)) and adding Seltrol spray oil at a concentration of 4 mg. spores per ml oil. Inoculum is then dispensed into gelatin capsules and applied with a vacuum pump. Four passes are made on both sides of the plant for uniformity. Plants are allowed twenty minutes to dry and then placed in a humidity cabinet (100% RH) in the dark for 20–24 h at 70° C. Plants are transferred to the greenhouse and evaluated 13 days later.

Tomato Late Blight (*Phytophthora infestans*)

Tomato (var. Pixie) seedlings, 3–4 inches tall are used for screening. A spore sunpension of the fungus is obtained by adding water to a jar of sporulating tomato leaves. The spore suspension is applied with a DeVilbiss atomizer at 8 to 10 psi air pressure onto the leaf undersurface until fine droplets are formed. Inoculated seedlings are placed in a humid environment (100% RH) at 60°–65° F. for 24 h, prior to being placed in a controlled temperature room in intermittent mist chambers at 20° C. and 90% RH. Treatment comparisons are made 4–5 days after inoculation.

Wheat Powdery Mildew (*Erysiphe graminis*)

"Victory-283" wheat seedlings (7 days old) are used as test plants. Wheat powdery mildew is cultured on wheat seedlings in a controlled temperature room at 65°–75° F. After chemical application, mildew spheres are shaken from culture plants onto seedlings. Inoculated seedlings are kept in the controlled temperature room and subirrigated. Disease control is rated 7 days after inoculation.

Cucumber Downey Mildew (*Pseudoperonspora cubensis*)

Cucumber (var. "Marketer") seedlings are grown for three weeks at 65°–75° F. in moderate light before use.

*Pseudoperonspora cubensis* is cultured in cucumber seedlings for 7 days at 65°–75° F. in moderate light (alternating light and dark periods). Spores are harvested by adding deionized water and shaking leaves in a quart jar. The spore suspension is filtered through cheesecloth to remove plant debris and adjusted to a concentration of $1 \times 10^5$ spores per ml.

The cucumber plants are inoculated by spraying the under side of the leaves with a DeVilbiss atomizer until small droplets are on the leaves. The inoculated leaves are incubated in a mist chamber for 24 hours at 70° F. and then subsequently incubated for 6–7 days in a controlled temperature room under mist at 65°–75° F.

Treatment comparisons are made 7 days after inoculation by estimating percent infected leaf surface. Symptoms appear as yellowing of the upper leaf surface and grey sporulating areas on the lower leaf surface.

Rice Sheath Blight (*Rhizoctonia solani*)

Seedlings of rice cultivar M-201 are grown in the greenhouse at 20°-30° C. in 2-inch pots in unsterilized soil with Turf-Builder for 14 days. Prior to the application of chemicals the plants are trimmed with scissors to a height of 4-5 inches.

Inoculum is produced in shake culture using the following procedure: autoclaved 500 ml wide-mouth flasks containing 150 ml potato dextrose broth are inoculated with a small piece of mycelium or a single sclerotium of *Rhizotonia solani* Kuhn. The flasks are placed on an electric shaker (1500 rpm) at 22° C. and a photoperiod of 14-16 hrs for 6 days. A slurry containing 100 ml deionized water, 20 g rice flour (no additives) and 23 g mycelium (wet weight) is prepared in a blender in the appropriate quantity to inoculate 2 inch pots with 4 ml/pot. Blend the mixture for about 1 min.

The slurry is dispensed into 2 inch pots using pipettes with an oversized opening at 4 ml/pot (10 ml/3 inch pot). While dispensing the inoculum, the pot should be tilted to insure uniform distribution of the slurry over the entire soil surface. During the inoculation the slurry is kept in suspension using a stirring plate at medium speed (high speed causes foaming).

Plants are put in a humidity cabinet at 28° C. for 43 hrs and then kept in a humidity cabinet at 25° C. for 53 hrs (photoperiod for both cases 16 hrs). The height of mycelial growth is observed as compared to the inoculated control plants. Records are kept as % control.

Rice Blast foliar treatments (*Pyricularia oryzae*)

Seedlings of the rice cultivar 'M-201' are grown in the greenhouse at 20°-30° C. in 2-inch pots containing unsterilized soil+Turf-Builder for 14 days. Rice plants are not trimmed before use.

Inoculum is produced in-vitro on oatmeal agar (50 g Gerber baby oatmeal, 20 bacto agar, 10 g bacto Dextrose, 1000 ml deionized water). The plates are inoculated with a mycelial plug (7-14 days old) of *Piricularia oryzae*. The outer edge of the dark region is used in the transfer. Inoculated plates are maintained at room temperature under constant fluorescent light.

*Pyricularia oryzae* plates 10-14 days old are flooded with a solution containing: 0.25 g Sodium oleate, 2 g gelatin, 1000 ml deionized water. The plates are scraped with a rubber policeman to release conidia, filter through a double layer of cheesecloth and adjust spore suspension of 25,000-30,000 spores/ml using a hemacytometer.

The spore suspension is sprayed on opposite sides of a double row of rice plants using a hand sprayer. Sufficient inoculum should be applied to achieve uniform distribution from soil to tip of rice leaves on opposite sides of each pot (approx. 50 ml/50 pots). Shake the sprayer after each pass to keep solution in suspension.

Inoculated plants are immediately placed in a humidity cabinet at 25° C. for 66 hrs prior to moving them to greenhouse bay 4 under the plastic tent. Plants are subirrigated but not allowed to stand in water more than 2 hrs. The plastic sides are lifted during work hrs and always closed at end of day.

After 76 hrs under greenhouse condition the bioassay plants are observed and the percent disease control (as compared to inoculated control) is estimated.

What is claimed is:

1. A method for controlling fungi which comprises incorporating into or onto the locus in need thereof a fungicidally effective amount of the compound of the following formula:

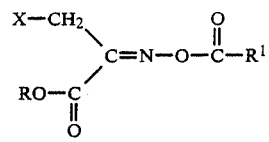

wherein X is halo; R is alkyl; $R^1$ alkyl, haloalkyl, alkenyl, haloalkenyl, alkoxy, haloalkoxy, lower alkyl amino, alkoxycarbonyl, alkoxycarbonylalkyl, aryl, aryloxy, aryloxyalkyl, aralkyl, aralkenyl, cycloalkyl, substituted aryl, substituted aryloxy and substituted aryloxyalkyl wherein the substituent is selected from one or more halo, lower alkyl, lower alkoxy, halo lower alkyl, or nitro substituents.

2. A method for controlling fungi which comprises incorporating into or onto the locus in need thereof a fungicidally effective amount of the compound of claim 1 the following formula:

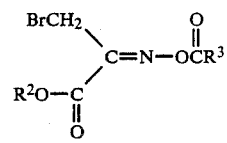

wherein $R^2$ is lower alkyl and $R^3$ is lower alkyl, halo lower alkyl, lower alkoxy, lower alkenyl, phenyl lower alkyl, halophenyl, trifluoromethylphenyl, nitrophenyl or methylamino.

3. A method for controlling fungi which comprises incorporating into or onto the locus in need thereof a fungicidally effective amount of the compound of claim 2 wherein $R^2$ is methyl or ethyl and $R^3$ is selected from chloromethyl, methyl, ethyl, propyl, isopropyl, butyl, 1-methylethenyl, methoxy, 2-, 3-, or 4-chlorophenyl 2-, 3-, or 4-fluorophenyl, ethenyl, or 1propenyl.

4. A method for controlling fungi which comprises incorporating into or onto the locus in need thereof a fungicidally effective amount of the compound of claim 3 wherein $R^2$ is ethyl and $R^3$ is 4-chlorophenyl.

5. A method for controlling fungi which comprises incorporating into or onto the locus in need thereof a fungicidally effective amount of claim 1 wherein X is bromo, R is ethyl and $R^1$ is 4-methylphenyl.

6. A method for controlling fungi which comprises incorporating into or onto the locus in need thereof a fungicidally effective amount of the compound of claim 1 wherein X is bromo, R is ethyl and $R^1$ is 3-methylphenyl.

7. A method for controlling fungi which comprises incorporating into or onto the locus in need thereof a fungicidally effective amount of the compound of claim 3 wherein $R^2$ is ethyl and $R^3$ is propyl.

8. A method for controlling fungi which comprises incorporating into or onto the locus in need thereof a fungicidally effective amount of the compound of claim 3 wherein $R^2$ is ethyl and $R^3$ is 1-methylethenyl.

9. A method for controlling fungi which comprises incorporating into or onto the locus in need thereof a fungicidally effective amount of the compound of claim 1 wherein X is bromo, R is ethyl and $R^1$ is 2-phenylethenyl.

10. A method for controlling fungi which comprises incorporating into or onto the locus in need thereof a fungicidally effective amount of the compound of claim 3 wherein $R^2$ is ethyl and $R^3$ is 4-fluorophenyl.

11. A method for controlling bacteria which comprises incorporating into or onto the locus in need thereof a bactericidally effective amount of the following formula:

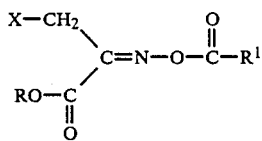

wherein X is halo; R is alkyl; $R^1$ alkyl, haloalkyl, alkenyl, haloalkenyl, alkoxy, haloalkoxy, lower alkyl amino, alkoxycarbonyl, alkoxycarbonylalkyl, aryl, aryloxy, aryloxyalkyl, aralkyl, aralkenyl, cycloalkyl, substituted aryl, substituted aryloxy and substituted aryloxyalkyl wherein the substituent is selected from one or more halo, lower alkyl, lower alkoxy, halo lower alkyl, or nitro substituents.

12. A method of controlling bacteria which comprises incorporating into or onto the locus in need thereof a bactericidally effective amount of the compound of claim 11 of the following formula:

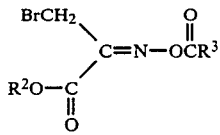

wherein $R^2$ is lower alkyl and $R^3$ is lower alkyl, halo lower alkyl, lower alkoxy, lower alkenyl, phenyl lower alkyl, halophenyl, trifluoromethylphenyl, nitrophenyl or methylamino.

13. A method of controlling bacteria which comprises incorporating into or onto the locus in need thereof a bactericidally effective amount of claim 12 wherein $R^2$ is methyl or ethyl and $R^3$ is selected from chloromethyl, methyl, ethyl, propyl, isopropyl, butyl, 1-methylethenyl, methoxy, 2-, 3- or 4-chlorophenyl, 2-, 3-, or 4-fluorophenyl, ethenyl, or 1-propenyl.

14. A method for controlling bacteria which comprises incorporating into or onto the locus in need thereof a bactericidally effective amount of claim 13 wherein $R^2$ is ethyl and $R^3$ is 4-chlorophenyl.

15. A method of controlling bacteria which comprises incorporating into or onto the locus to in need thereof a bactericidally effective amount of the compound of claim 11 wherein X is bromo, R is ethyl and $R^1$ is 4-methylphenyl.

16. A method of controlling bacteria which comprises incorporating into or onto the locus in need thereof a bactericidally effective amount of the compound of claim 11 wherein X is bromo, R is ethyl and $R^1$ is 3-methylphenyl.

17. A method of controlling bacteria which comprises incorporating into or onto the locus in need thereof a bactericidally effective amount of claim 13 wherein $R^2$ is ethyl and $R^3$ is propyl.

18. A method for controlling bacteria which comprises incorporating into or onto the locus in need thereof a bactericidally effective amount of claim 13 wherein $R^2$ is ethyl and $R^3$ is 1-methylethenyl.

19. A method of controlling bacteria which comprises incorporating into or onto the locus in need thereof a bactericidally effective amount of the compound of claim 11 wherein X is bromo, R is ethyl and $R^1$ is 2-phenylethyl.

20. A method for controlling bacteria which comprises incorporating into or onto the locus in need thereof a bactericidally effective amount of claim 13 wherein $R^2$ is ethyl and $R^3$ is 4-fluorophenyl.

* * * * *